United States Patent [19]

Kaetsu et al.

[11] 4,310,397

[45] Jan. 12, 1982

[54] POLYMER COMPOSITION CONTAINING A PHYSIOLOGICALLY ACTIVE SUBSTANCE

[75] Inventors: Isao Kaetsu; Masaru Yoshida; Masaharu Asano, all of Takasaki, Japan

[73] Assignee: Japan Atomic Energy Research Institute, Tokyo, Japan

[21] Appl. No.: 120,896

[22] Filed: Feb. 12, 1980

[30] Foreign Application Priority Data

Feb. 19, 1979 [JP] Japan .................................. 54-017298

[51] Int. Cl.$^3$ ........................ C08F 2/48; A61K 31/74; A61K 31/78
[52] U.S. Cl. ................................ 204/159.22; 424/78; 424/81; 260/37 R
[58] Field of Search ....................... 204/159.22, 159.23; 424/78, 81

[56] References Cited

U.S. PATENT DOCUMENTS

| | | | |
|---|---|---|---|
| 3,577,512 | 5/1971 | Shepherd et al. | 424/81 |
| 3,767,790 | 10/1973 | Guttag | 424/81 |
| 4,025,391 | 5/1977 | Kawashima et al. | 204/159.22 |
| 4,269,821 | 5/1981 | Kreuter et al. | 424/81 |

*Primary Examiner*—Melvyn I. Marquis
*Assistant Examiner*—A. H. Koeckert
*Attorney, Agent, or Firm*—Posnack, Roberts, Cohen & Spiecens

[57] ABSTRACT

A polymer composition containing a physiologically active substance and being capable of releasing it at a controlled rate can be prepared by contacting 10 parts, by weight, of one or more polymerizable monomers and 0.1 to 30 parts, by weight, of one or more physiologically active substances and irradiating them with light or an ionizing radiation while maintaining the system in an anhydrous condition and in airless state.

5 Claims, No Drawings

POLYMER COMPOSITION CONTAINING A PHYSIOLOGICALLY ACTIVE SUBSTANCE

BACKGROUND OF THE INVENTION

1. Field of the Invention

The present invention relates to a process for preparing a polymer composition containing a physiologically active substance. More particularly, the present invention relates to a process for preparing a polymer composition containing a physiologically active substance and having a property of releasing the substance at a controlled rate.

2. Prior Art

The present inventors have previously invented a process for preparing a polymer composition having a property of releasing a physiologically active substance at a controlled rate which comprises contacting a polymerizable monomer and the physiologically active substance and irradiating them with light or an ionizing radiation to polymerize the monomer (Japanese Patent Application No. 27,109/78, U.S. Ser. No. 018,617) and, further, on the basis of this invention, have accomplished a series of inventions of a process for preparing a polymer composition having the same property which comprises dropping or injecting a mixture of one or more monomers vitrificable at low temperatures containing a high molecular weight substance and the physiologically active substance into a medium to make the mixture into a shape of spherical structure and irradiating it with light or an inoizing radiation (Japanese Patent Application No. 51,239/78, U.S. Ser. No. 018,617), a process for preparing a polymer composition in which the elution rate of the physiologically active substance is controlled by pH which comprises irradiating a uniform mixture of a polymer soluble in a pH within a certain range, a polymerizable monomer and the physiologically active substance with light or an ionizing radiation to polymerize the monomer (Japanese Patent Application No. 105,306/78, U.S. Ser. No. 18,617), a process for preparing a polymer composition having the same property which comprises mixing a polymerizable monomer and physiologically active substance in the presence or absence of crystallizable substance, adding an adsorbent thereto and irradiating it with light or an ionizing radiation (Japanese Patent Application No. 106,097/78, U.S. Ser. No. 18,617), and a process for preparing a polymer composition containing an antitumour agent and having a property of releasing it at a controlled rate which comprises mixing a polymerizable monomer with two or more antitumour agents, or one or more antitumour agents and a substance promoting antitumour effect and irradiating the mixture with light or an ionizing radiation (Japanese Patent Application No. 146,411/78, U.S. Ser. No. 095,496). However, a physiologically active substance is generally broken or decomposed by the action of radiation and thereby its activity lowers. In order to restrain the lowering of activity, in the processes of these inventions, the irradiation has been performed at ordinary temperatures or in a lower temperature domain as below 0° C. Therefore, the monomer to be used had to be a monomer polymerizable at low temperature.

SUMMARY OF THE INVENTION

As the result of research on the condition in the irradiation, the present inventors have found that the lowering of the activity of the physiologically active substance is promoted by the existence of oxygen in the reaction system and the activity is scarcely lowered when the radiation irradiation is performed under a vacuum of $10^{-3}$ to $10^{-4}$ mmHg without oxygen and also the polymerization of polymerizable monomer is promoted by the removal of oxygen, and that it is possible to avoid the lowering of the activity of physiologically active substance caused by the irradiation in an anhydrous system in which water is completely removed from the reaction system, even in a temperature domain above 0° C. The present inventors have, on the basis of these discoveries, accomplished the present invention which comprises a process for preparing a polymer composition containing a physiologically active substance which comprises contacting one or more polymerizable monomers and one or more physiologically active substances and irradiating them with light or an ionizing radiation while maintaining the system in an anhydrous state and in an airless state.

DETAILED DESCRIPTION OF THE PREFERRED EMBODIMENTS

The polymer composition containing a physiologically active substance according to the process of the present invention can be in any form, such as powder, film, sphere, rod or block. However, generally the physiologically active substance is not soluble but only dispersed in a polymerizable monomer and so, as an ideal controlled releasing agent, it is desired that the encapsulation is completed in a state that the physiologically active substance is uniformly dispersed through the polymer of polymerizable monomer. When the dispersion is not uniform the elution of physiologically active substance from the polymer composition cannot be satisfactorily controlled and the reproducibility is in danger of being difficult.

In order to disperse a physiologically active substance which is insoluble in a polymerizable monomer in a polymer uniformly, there is contemplated a process for preparing a polymer composition releasing the physiologically active substance contained at a controlled rate by coating the surface of the physiologically active substance with the minimum amount of polymerizable monomer and polymerizing the monomer. And in the case of a physiologically active substance which is relatively easily soluble in a polymerizable monomer, such as, for example ammonium chloride, creosote, ibuprofen, etc., the preparation of the controlled releasing agent is easy and any method or means of dispersion can be used since the encapsulation of physiologically active substance can be performed in an anhydrous system.

When combining one or more of any polymerizable monomers properly, a polymer soluble or insoluble in an acidic or basic aqueous solution can be obtained at will. For example, a polymer obtained by polymerizing dimethylaminoethyl methacrylate and methacrylic acid ester in an appropriate ratio is soluble in an acidic liquid (for example gastric juice) while a polymer obtained by polymerizing methacrylic acid and methacrylic acid ester in an appropriate ratio is soluble in a basic liquid (for example intestinal juice). But a polymer obtained by polymerizing one or more polymerizable monomers having an appropriate number of functional groups (for example vinyl group) alone or in combination, for example, the copolymer of 2-hydroxyethyl methacrylate and diethyleneglycol dimethacrylate is not soluble in either acidic or basic solutions.

In the method of obtaining polymers having various properties by various combinations as above described, the means of preparing the polymers is limited to a radiation polymerization method, although the kind, composition and components are optional. Further, one method of controlling the elution of a physiologically active substance from a polymer composition is to polymerize a polymerizable monomer in coexistence in an inert solvent such as polyethylene glycol, hydroxypropyl cellulose, etc. In such polymerization a void pore space is formed within the polymer by the elution of inert solvent. The void pore space is an important factor for controlling the elution of physiologically active substances since the void pore space can be controlled by selecting the kind and concentration of the inert solvent.

The present invention is not limited to a radiation of ordinary temperature or a lower temperature domain as 0° C., differing from the processes of the above described prior inventions, Therefore, there is no necessity for using a polymerizing catalyst and solvent normally necessary for polymerization in such low temperature domain, and so these are not mixed as impurities in the polymer composition. In addition, the present invention can be characterized in that the radiation sterilization of the polymer can be effected and that the polymerization and the encapsulation of the physiologically active substance are performed simultaneously so that the resulting composition is stable.

Polymerizable monomers suitable for use in the present invention include:
hydroxyethyl methacrylate, hydroxyethyl acrylate, hydroxypropyl methacrylate, hydroxyprophyl acrylate, diethylene glycol monoacrylate, diethylene glycol monomethacrylate, dipropylene glycol monoacrylate, dipropylene glycol monomethacrylate, triethylene glycol monoacrylate, triethylene glycol monomethacrylate, tripropylene glycol monoacrylate, tripropylene glycol monomethacrylate, tetraethylene glycol monoacrylate, tetraethylene glycol monomethacrylate, tetrapropylene glycol monoacrylate, tetrapropylene glycol monomethacrylate, polypropylene glycol monoacrylate, polypropylene glycol monomethacrylate, polyethylene glycol monoacrylate, polyethylene glycol monoethacrylate, methoxydiethylene glycol acrylate, methoxydiethylene glycol methacrylate, methoxydipropylene glycol acrylate, methoxypropylene glycol methacrylate, ethoxydiethylene glycol acrylate, ethoxydiethylene glycol methacrylate, ethoxydipropylene glycol acrylate, ethoxydipropylene glycol methacrylate, propoxydiethylene glycol acrylate, propoxydiethylene glycol methacrylate, propoxydipropylene glycol acrylate, propoxydipropylene glycol methacrylate, butoxydiethylene glycol acrylate, butoxydiethylene glycol methacrylate, butoxydipropylene glycol acrylate, butoxydipropylene glycol methacrylate, methoxytriethylene glycol acrylate, methoxytriethylene glycol methacrylate, methoxytripropylene glycol acrylate, methoxytripropylene glycol methacrylate, ethoxytriethylene glycol acrylate, ethoxytriethylene glycol methacrylate, ethoxytripropylene glycol acrylate, ethoxytripropylene glycol methacrylate, propoxytriethylene glycol acrylate, propoxytriethylene glycol methacrylate, propoxytripropylene glycol acrylate, propoxytripropylene glycol methacrylate, butoxytriethylene glycol acrylate, butoxytriethylene glycol methacrylate, butoxytripropylene glycol acrylate, butoxytripropylene glycol methacrylate, methoxytetraethylene glycol acrylate, methoxytetraethylene glycol methacrylate, methoxytetrapropylene glycol acrylate, methoxytetrapropylene glycol methacrylate, ethoxytetraethylene glycol acrylate, ethoxytetraethylene glycol methacrylate, ethoxytetrapropylene glycol acrylate, ethoxytetrapropylene glycol methacrylate, propoxytetraethylene glycol acrylate, propoxytetraethylene glycol methacrylate, propoxytetrapropylene glycol acrylate, propoxytetrapropylene glycol methacrylate, butoxytetraethylene glycol acrylate, butoxytetraethylene glycol methacrylate, butoxytetrapropylene glycol acrylate, butoxytetrapropylene glycol methacrylate, methoxypolyethylene glycol acylate, methoxypolyethylene glycol methacrylate, methoxypolypropylene glycol acrylate, methoxypolypropylene glycol methacrylate, ethoxypolyethylene glycol acrylate, ethoxypolyethylene glycol methacrylate, ethoxypolypropylene glycol acrylate, ethoxypolypropylene glycol methacrylate, propoxypolyethylene glycol acrylate, propoxypolyethylene glycol methacrylate, propoxypolypropylene glycol acrylate, propoxypolypropylene glycol methacrylate, butoxypolyethylene glycol acrylate, butoxypolyethylene glycol methacrylate butoxypolypropylene glycol acrylate, butoxypolypropylene glycol methacrylate; and, in addition, include:
methyl methacrylate, ethyl methacrylate, glycidyl methacrylate, propyl methacrylate, butyl methacrylate, isobutyl methacrylate, benzyl methacrylate, cyclohexyl methacrylate, 2-ethylhexyl methacrylate, hexyl methacrylate, lauryl methacrylate, methyl acrylate, ethyl acrylate, glycidyl acrylate, propyl acrylate, butyl acrylate, isobutyl acrylate, benzyl acrylate, cyclohexyl acrylate, 2-ethylhexyl acrylate, hexyl acrylate, lauryl acrylate, acrylic acid, acrylamide, acrylonitrile, vinyl acetate, vinyl propionate, vinyl butyrate, vinyl toluene, styrene, vinyl benzene, vinyl pyrrolidone, vinyl carbazol, methacrylic acid, methacrylamide, methacrylonitrile, triallyl cyanurate, diallyl phthalate, diallyl maleate, diallyl itaconate, diallyl succinate, diallyl isophthalate, triacryl formal, dipropargyl maleate, trimethylolpropane trimethacrylate, trimethylolpropane triacrylate, neopentyl glycol dimethacrylate, neopentyl glycol diacrylate, diethylene glycol dimethacrylate, diethylene glycol diacrylate, triethylene glycol dimethacrylate, triethylene glycol diacrylate, tetraethylene glycol dimethacrylate, tetraethylene glycol diacrylate, polyethylene glycol dimethacrylate, polyethylene glycol diacrylate, hexanediol diacrylate, hexanediol dimethacrylate, pentanediaol diacrylate, pentanediol dimethacrylate, butanediol diacrylate, butanediol dimethacrylate, ethylene glycol diacrylate, ethylene glycol dimethacrylate.

Inert solvents used in the present invention include:
ethylene glycol, polyethylene glycol, cyclohexane, benzene, acetic acid, propionic acid, butyric acid, crotonic acid, maleic acid, succinic acid, sorbic acid, itaconic acid, liquid paraffin, ethanol, edible oils and fats, and the like, although any solvent inert in the interior of the living body may be used.

Physiologically active substances which can be used in the present invention include:

acetylchloline, noradrenalin, serotanin, callicrein, gastrin, secretin, adrenalin, insulin, glucagon, ACTH, growth hormone, genadotropic hormone, oxytocin, vasopressin, thyroxin, testicular hormone (testosterone), ovarian hormone (estradiol), corpus luteum hormone, luteal hormone (progesteroune), adrenocortical hormone, prostaglandin, various antihistaminic agents, antihypertensives, vasodilators, vasoprotectors, stomachics and digestives, anti-diarrheals and intestinal absorbers, contraceptives, antiseptics and disinfectants for derma, agents for dermatozoonosis, antiphlogistic, acetysalicyclic acid, ibuprofen, phenacetin, mefenamic acid, maproxen, tiaramide, indomethacin, vitamins, varous enzymes, antitumor agents (bleomycin, sarcomycin, actinomycin D, cyclophosphamide, nitrogen mustard, triethylene thiophosphoramide, mercaptopurine, methotrexate, 5-fluorouracil, mitomycin C, carzinophilin, chromomycin $A_3$, 1-2(2-tetrahydro-furyl)-5-fluorouracil, etc.), radiopharmaceuticals, antibiotics (streptomycins, chloramphenicols, tetracyclines, ethythromycins, trichomycins, bacitracins, colistins, polymixins, gramicidins, penicillins, griseofulvins, etc.), sulfanilamide and its derivatives, antituberculosis drugs (TB preparations), antisyphilitics, antilep, varous biological preparations (vaccines, antiserums, toxins and antitoxins, etc.), amebicides, authelmintics, ataraxics, ophthalmological preparations (anticataract agents, antiglancoma agents, etc.), various fish drugs, agricultural drugs, interferon, auxin, gibberelline, cytokinin, absinthic acid, other phytohormones, sex pheromone, aggregation pheromone, alarm pheromone, trail pheromone, cast pheromone, other pheromones, various natural insecticidal substances (pyrethroid, rotinoid, nicotinoid, etc.), attractant, repellent, etc.

DESCRIPTION OF PREFERRED EMBODIMENTS

The present invention will be described in greater detail with reference to the following Examples:

In the process of the present invention, the irradiation is performed in an anhydrous condition. An extremely small quantity of water existing in the polymerizable monomer was removed by passing the monomer through a column filled with a drying agent such as Molecular Sieves 4A, silica gel, active carbon, active alumina, etc., and the physiologically active substance was dried by vacuum drying or lyophilization. The elution test of the physiologically active substance from the polymer composition obtained was carried out using 1,000 ml of liquid medium in a rotatable basket at 100 rpm and at a temperature of 37° C. according to USP XIX.

EXAMPLES 1 TO 5

1.2 g of aminophylline powder was added to 1 g of mixed polymerizable monomers of dimethylaminoethyl methacrylate and methyl methacrylate in an appropriate composition. Thereafter the reaction system was deaerated ($10^{-3}$ mmHg), and then was irradiated with $\gamma$ ray from $^{60}$Co at a dose rate of $5\times10^5$ R/hr at 28° C. for 3 hours in such a condition that aminophylline is covered uniformly with the polymerizable monomers to obtain a polymer composition containing aminophylline. The elution of aminophylline from the polymer composition crushed to 3.5 to 5.0 mm in size was held in a liquid medium at a pH of 3. The results are shown in Table 1.

TABLE 1

Elution of aminophylline from dimethylaminoethyl methacrylate-methyl methacrylate copolymer

| | Composition of polymerizable monomer | | Amount of aminophylline eluted from liquid medium at a pH of 3, % Time elapsed after test started, hour | | | | | |
|---|---|---|---|---|---|---|---|---|
| | DAEMA % | MMA % | 0.5 | 1 | 2 | 4 | 8 | 12 |
| Example | | | | | | | | |
| 1 | 100 | 0 | 4.6 | 12.3 | 32.4 | 59.2 | 100 | — |
| 2 | 70 | 30 | 3.1 | 5.2 | 14.6 | 48.3 | 92.4 | 100 |
| 3 | 50 | 50 | 1.3 | 3.4 | 4.5 | 9.6 | 14.4 | 26.8 |
| 4 | 30 | 70 | 2.2 | 4.8 | 7.3 | 14.2 | 23.2 | 38.4 |
| 5 | 0 | 100 | 5.1 | 8.2 | 14.3 | 22.2 | 34.1 | 44.4 |
| Comparative Example | | | | | | | | |
| 1 | 70 | 30 | 2.1 | 3.6 | 6.2 | 11.2 | 17.6 | 24.6 |
| 2 | 30 | 70 | 1.8 | 4.0 | 6.7 | 13.4 | 20.6 | 36.2 |

DAEMA: Dimethylaminoethyl methacrylate
MMA: Methyl methacrylate
Note 1.
Comparative Examples 1 and 2 were carried out in a liquid medium at a pH of 6.
Note 2.
In case the amount of dimethylaminoethyl methacrylate is above 45%, the copolymer obtained is completely soluble in the liquid medium of a pH of 3 and the solubility of the copolymer increases with the percentage of dimethylaminoethyl methacrylate.

EXAMPLES 6 TO 10

0.32 g of Tolbutamide was added to 0.3 g of mixed polymerizable monomers of methyl acrylate and methacrylic acid in an appropriate composition, and thereafter the reaction system was deaerated and then was irradiated with $\gamma$ ray from $^{60}$Co at a dose rate of $1\times10^6$ R/hr at 25° C. for 2 hours under the condition that tolbutamide is covered uniformly with the polymerizable monomers to obtain a tablet of polymer composition containing tolbutamide of 8 mm in diameter and 4 mm in height. The elution of tolbutamide from the polymer composition tablet was held in a liquid medium of a pH of 3.0. The results are shown in Table 2.

TABLE 2

Elution of tolbutamide from methyl acrylate and methacrylate acid copolymer

| | Composition of polymerizable Monomer | | Amount of tolbutamide eluted from a liquid medium of a pH of 7.0, % Time elapsed after test started, hour | | | | | |
|---|---|---|---|---|---|---|---|---|
| | Methyl acrylate % | Methacrylic acid % | 0.5 | 1 | 2 | 4 | 8 | 12 |
| Example | | | | | | | | |
| 6 | 100 | 0 | 4.2 | 6.4 | 14.2 | 22.4 | 41.3 | 50.3 |
| 7 | 70 | 30 | 14.3 | 22.1 | 30.4 | 44.3 | 57.8 | 89.4 |
| 8 | 50 | 50 | 17.6 | 27.3 | 36.8 | 50.2 | 78.4 | 96.2 |
| 9 | 30 | 70 | 18.4 | 29.3 | 58.9 | 88.4 | 100 | |
| 10 | 0 | 100 | 32.1 | 54.1 | 84.2 | 100 | | |
| Comparative Example | | | | | | | | |
| 3 | 70 | 30 | 10.2 | 18.6 | 27.3 | 39.1 | 51.2 | 69.9 |
| 4 | 30 | 70 | 4.1 | 7.6 | 12.1 | 19.4 | 26.9 | 33.4 |

Note 1.
Comparative Examples 3 and 4 were carried out in a liquid medium of a pH of 3.0.
Note 2.
In case the amount of methacrylic acid is above 60%, the copolymer obtained is completely soluble in the liquid medium of a pH of 7.0 and the solubility of the copolymer increases with the percentage of methacrylic acid.

EXAMPLE 11

1.0 g of methyl salicylate, 0.4 g of 1-menthol, 0.1 g of peppermint oil, 0.4 g of dl-camphor and 0.2 g of thymol were added to 2 g of polymerizable monomer of 80% hydroxyethyl acrylate and 20% diethylene glycol dimethacrylate, and were cast using an inorganic glass plate to obtain a filmy polymer of 2 mm in thickness in which the chemicals are uniformly dispersed within the film, and which was then irradiated at $\gamma$ ray from $^{60}$Co with a dose rate of $4\times10^5$ R/hr at 31° C. for 3 hours.

The resulting filmy polymer composition was excellent in elasticity and flexibility and was not soluble regardless of the pH of the liquid medium. The results of the elution of chemicals from the filmy polymer composition are shown in Table 3.

TABLE 3

Elution of chemicals from filmy copolymer composition of 80% hydroxyethyl acrylate and 20% diethylene glycol dimethacrylate

| | Amount of chemicals eluted from filmy polymer composition after elution test started. Time elapsed after test started, hour | | | |
|---|---|---|---|---|
| | 1 % | 5 % | 10 % | 20 % |
| Methyl salicylate | 15 | 38 | 69 | 92 |
| l-menthol | 8 | 26 | 51 | 87 |
| Peppermint oil | 21 | 47 | 81 | 100 |
| dl-camphor | 19 | 41 | 74 | 98 |
| Thymol | 7 | 21 | 46 | 79 |

EXAMPLE 12

3 g of trimethylolpropane trimethacrylate, 1 g of polyethylene glycol #200 and 2 g of creosote were mixed uniformly and thereafter the resulting mixture solution was filled into a polyethylene tube of 3 mm in inner diameter and was irradiated at $\gamma$ ray from $^{137}$Cs with a dose rate of $3\times10^5$ R/hr at 26° C. for 4 hours.

The polymer composition so obtained was cut to a chip of 5 mm in length. This polymer composition has a porous structure by the elution of the polyethylene glycol #200. The elution of creosote from the polymer composition was carried out in pure water (pH 6.0), and creosote was eluted at a uniform rate for 10 days and approximately 87% in total was eluted. For comparison, in the case of preparing a similar chip-like polymer without making polyethylene glycol #200 coexistent in the system, the elution of creosote therefrom was only 41% for 10 days.

What is claimed is:

1. A process for preparing a polymer composition containing a physiologically active substance which is released at a controlled rate, said process comprising contacting 10 parts, by weight, of at least one polymerizable monomer and 0.1 to 3 parts, by weight, of at least one physiologically active substance and irradiating them with light or an ionizing radiation while maintaining the system in an anhydrous condition and in an airless state such that in the produced polymer composition the physiologically active substance is capable of being released at a controlled rate.

2. The process as set forth in claim 1 in which said contact is effected in the presence of 0.1 to 10 parts, by weight, of inert solvent.

3. The process as set forth in claim 1 or 2 in which said airless state is a vacuum below $10^{-2}$ mmHg.

4. The process as set forth in claim 1 or 2 in which said ionizing radiation is $\gamma$ ray from $^{60}$Co or $^{137}$Cs or $\beta$ ray from $^{90}$Sr.

5. The process as set forth in claim 1 wherein the controlled rate of release of the physiologically active substance is substantially uniform over a period of time.

* * * * *